US00PP18039P3

(12) United States Plant Patent
Jeske

(10) Patent No.: US PP18,039 P3
(45) Date of Patent: Sep. 18, 2007

(54) HOP PLANT NAMED 'SUMMIT'

(50) Latin Name: *Humulus Lupulus L*
Varietal Denomination: Summit

(75) Inventor: Roger Jeske, Prosser, WA (US)

(73) Assignee: American Dwarf Hop Assoc., Moxee, WA (US)

( * ) Notice: Subject to any disclaimer, the term of this patent is extended or adjusted under 35 U.S.C. 154(b) by 4 days.

(21) Appl. No.: 11/236,165

(22) Filed: Sep. 26, 2005

(65) Prior Publication Data

US 2007/0074321 P1 Mar. 29, 2007

(51) Int. Cl.
*A01H 5/00* (2006.01)

(52) U.S. Cl. ..... Plt./236

(58) Field of Classification Search ..... Plt./236
See application file for complete search history.

*Primary Examiner*—Kent Bell
*Assistant Examiner*—Annette H Para
(74) *Attorney, Agent, or Firm*—Wells St. John P.S.

(57) ABSTRACT

A new variety of hop is described and which is characterized principally as to novelty by being semi-dwarf in stature; and which further produces cones having a high percentage of alpha-acids, high alpha/beta ratio and excellent storage stability of alpha-acids.

3 Drawing Sheets

BACKGROUND OF THE NEW VARIETY

The present invention relates to a new, novel and distinct variety of hop 'Humulus lupulus L' and which has been denominated varietally, hereinafter, as 'Summit'.

ORIGIN

Hops are grown commercially and are principally used in the brewing industry to add bitterness and flavor to beverages such as beer. Lupulin glands found inside female hop cones provide the resins and essential oils which are the primary component of the hop flavor which is imparted to such beverages.

New hop varieties are typically evaluated for their growing characteristics, hop cone yields, disease resistance, and the chemical composition of the resins and essential oils contained within the hop cone glands. As should be understood, only female hop plants produce cones containing the lupulin glands, and thus only female hop plants have any significant commercial value.

The present hop plant was derived from a multitude of hop plants resulting from a controlled cross-pollination which was conducted during the summer of 2000. The aforementioned cross-pollination was performed between a non-patented, female hop plant owned by the inventor, and commonly referred to as 'Lexus'; with a non-patented, male hop plant. The female parent 'Lexus' had previously been derived from a controlled cross-pollination which was conducted during the summer of 1999. In this regard, the female parent 'Lexus' was derived from a cross-pollination conducted between the female hop plant 'Zeus' which is commercially available, and non-patented; and a non-patented male hop plant designated as USDA 19058 m. The male parent had resulted from an earlier controlled cross-pollination conducted during the summer of 1999 between the female hop plant 'Zeus', first mentioned, above; and a non-patented male hop plant which is named '(Nugget X open)$_m$' and which was owned by the inventor. This same male hop plant was earlier selected from a number of seedlings arising from the seeds which were collected from the Nugget hop cones. The Nugget hop cones had been pollinated and originated from a commercial hop field which is located near Harrah, Wash.

The controlled cross-pollination program resulting in the creation of the new hop variety of the present application was performed during the 2000 growing season by the inventor at his personal residence which is located in Yakima, Wash. The inventor discovered the new variety of hop during the 2001 growing season among the numerous hop plants then growing at his residence, and which had been germinated from seeds resulting from the above described controlled cross-pollination program. The seeds from the cross-pollination first referenced, above, were planted in the inventor's greenhouse during January, 2001. Thereafter, the most vigorous plants resulting from the aforementioned cross-pollination were selected and planted by the inventor in his experimental hop field which is located in Yakima, Wash. These plants were grown on twine attached to a 10 foot high trellis during the 2001 and 2002 growing seasons.

Subsequent chemical analysis and field observations made in 2002 and thereafter revealed the new hop plant 'Summit' had an unusually high percentage of alpha acids; short internode lengths which indicated a semi-dwarf characteristic; a lack of powdery mildew; and a reasonably projected per acre cone yield when grown on a low trellis. During the 2003 growing season, the 'Summit' hop plant was grown in two geographically different locations with no powdery mildew observed. Further, the production of alpha-acids were quite high as calculated at both locations. The plants growing at the two different geographical locations constituted the first asexual reproduction of the present variety. Based upon the field observations performed, and the chemical and analytical data collected during testing and evaluation of the variety during the 2002–2005 growing seasons, it appears that the second and third generation 'Summit' hop plants demonstrate genetic stability with respect to the new variety's novel characteristics of unusually high alpha-acids yields; very high alpha/beta ratios; excellent storage stability of alpha acids; and powdery mildew resistance.

In relative comparison to the unpatented commercially available 'Zeus' variety, the present variety 'Summit' is considered to be a semi-dwarf which makes it a better prospect for growth on low trellis arrangements. Further, the variety 'Summit' is resistant to the powdery mildew strains found in the Yakima Valley, and has much better storage stability of alpha acids and has a higher alpha/beta acid ratio in comparison to the variety 'Zeus.'

BRIEF DESCRIPTION OF THE DRAWINGS

The accompanying drawings which are provided are color photographs of the present variety.

Figure 1:
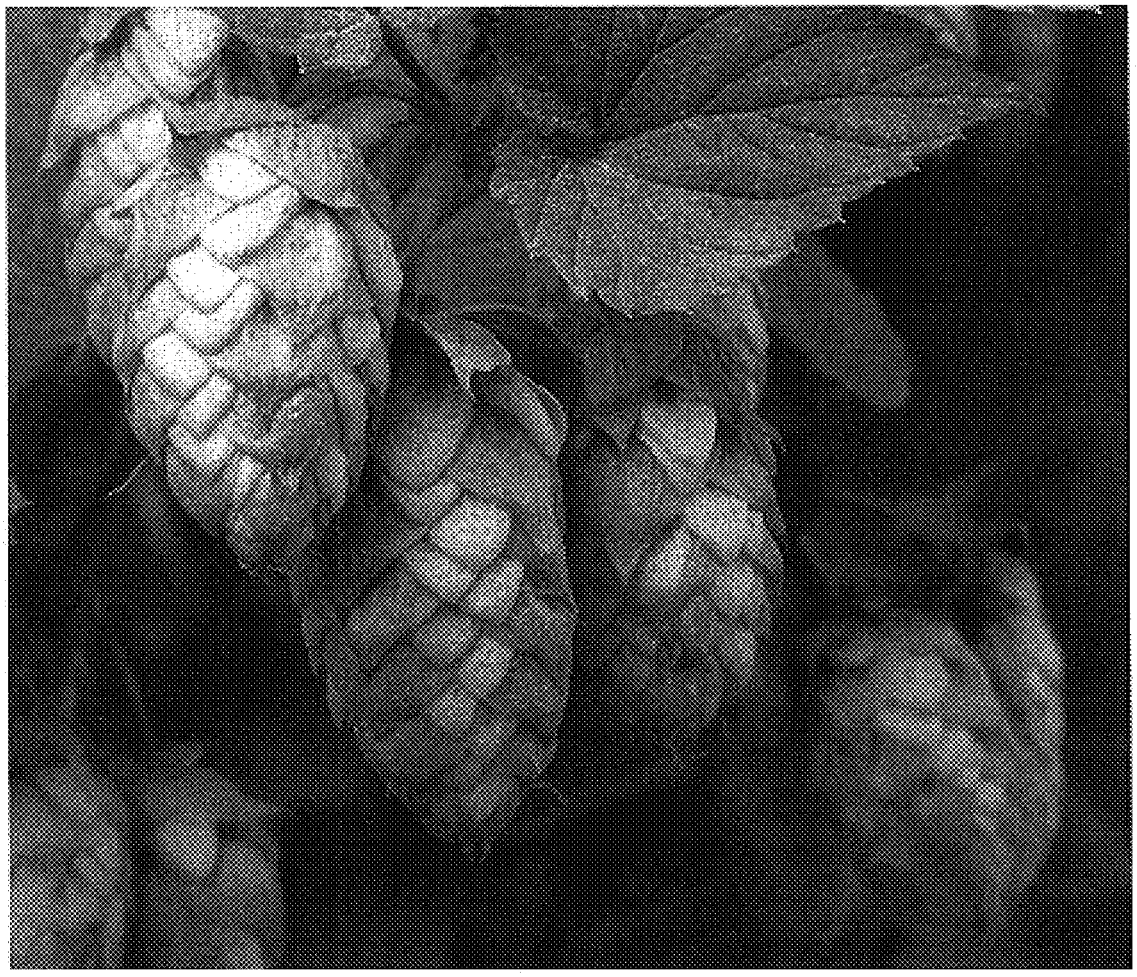
FIG. 1 shows several whole cones of the present variety.
Figure 2:
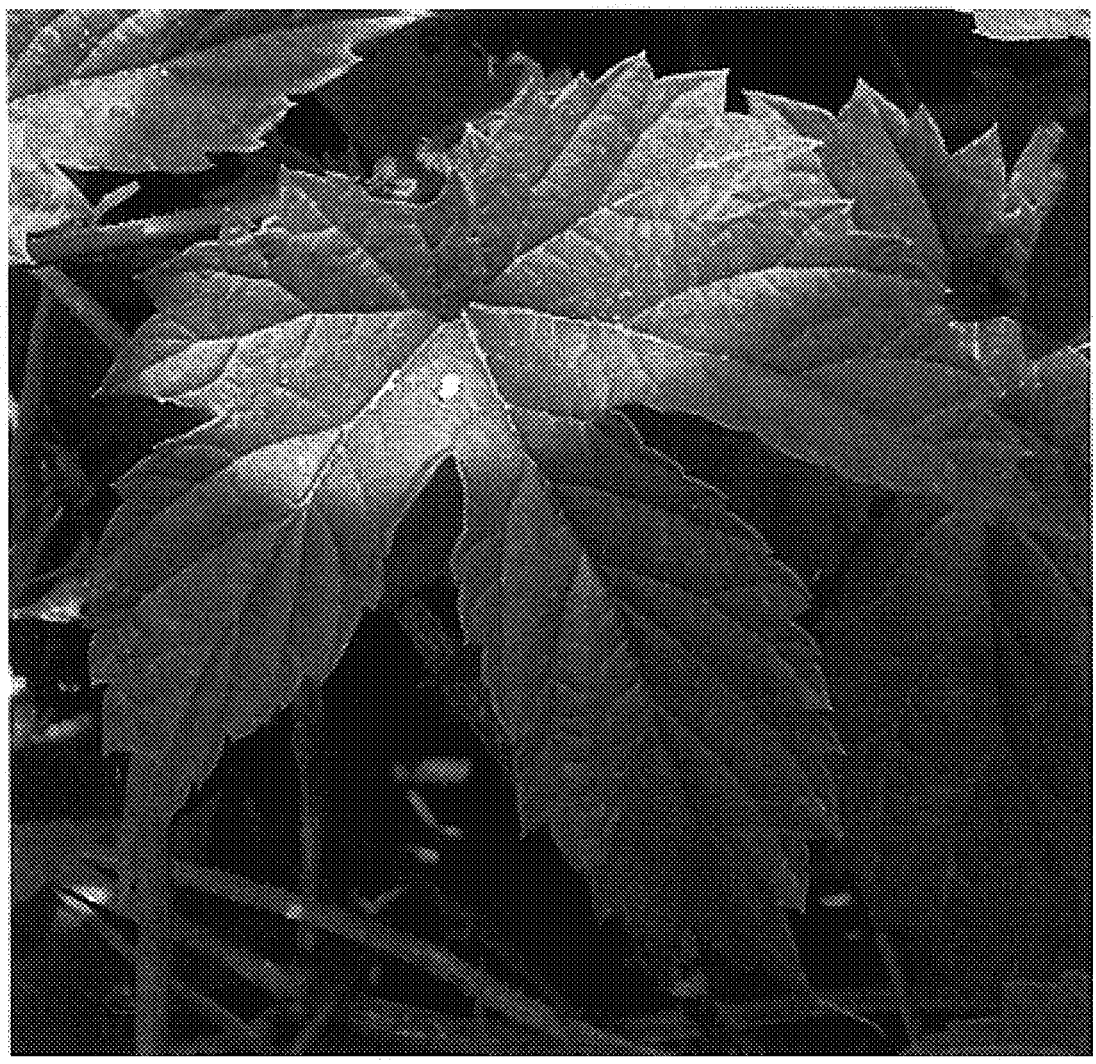
FIG. 2 depicts a mature vine leaf of the present variety.
Figure 3:
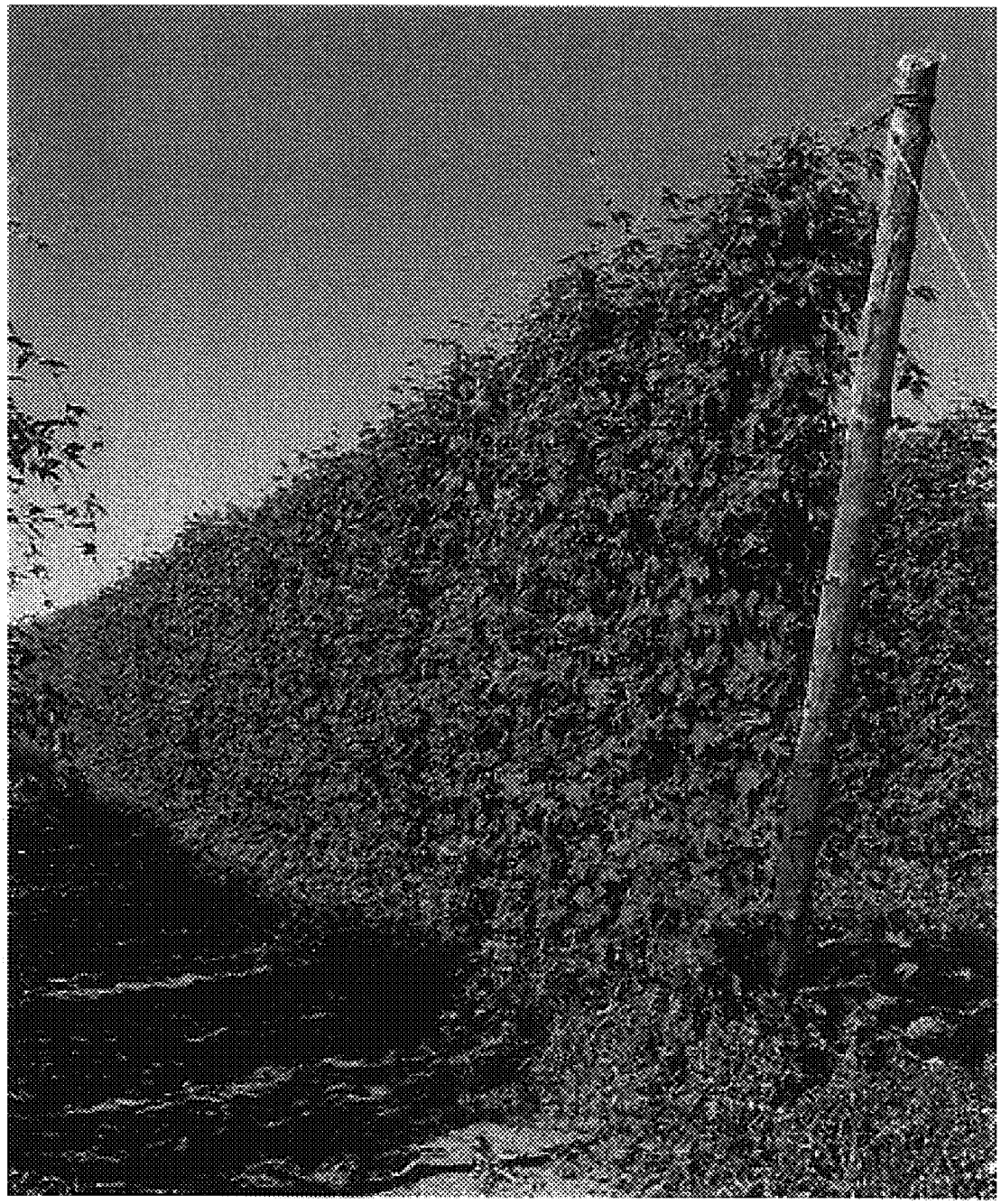
FIG. 3 depicts the growing characteristics of the present variety when grown on a low trellis (approximately 10 ft.).

The colors are as nearly true as is reasonably possible in color representations of this type. Due to chemical development and processing and printing, the leaves, and cones depicted in these photographs may or may not be accurate when compared to the actual specimen. For this reason, future color references should be made to the color plates (Royal Horticultural Society), and descriptions provided hereinafter.

DETAILED DESCRIPTION

Referring more specifically to the details of this new and distinct variety of hop plant, the following has been observed under the ecological conditions prevailing near Moxee, Wash. All major color code designations are by reference to the R.H.S. Colour Chart, $4^{th}$ Edition provided by The Royal Horticultural Society of Great Britain.

PLANT

*Generally.*—Considered semi-dwarf, and maintaining a height of approximately 14 to 16 feet. The present variety is a perennial producing annual climbing bines and a perennial crown. The present variety does not self-pollinate.

*Bines.*—Growth characteristic — Bines of the present variety climb in a clockwise direction with the aid of tricomes.

*Bine.*—Color — Green, (RHS 146C). The color of the bine is not distinctive of the present variety. Further, six light brownish purple stripes typically appear on the bine.

*Bine.*—Thickness — The bine of a mature hop plant may have a dimension of about ⅜ to about ½ of an inch in thickness when measured at a distance of approximately 6 feet above ground level.

*Laterals.*—Position — Considered caulous and substantially evenly spaced along the main bine. Laterals of the present variety grow from auxiliary buds at each node along the main bine.

*Laterals.*—Growth Habit — Generally speaking, Laterals grow from auxiliary buds at each node along the main bine. Inflorescences develop from axils of the Laterals. Each inflorescence becomes a hop cone at maturity.

*Laterals.*—Length — Considered shorter than most commercial varieties. The typical lateral length ranges from about 18 to about 30 inches.

*Internodes.*—Length — The present variety has internode lengths of approximately 1½ to about 4 inches. Typically, laterals will have approximately 6 to about 8 internodes each.

*Stems.* —Generally — The annual stems of the present variety grow from the crown and rhizomes of the plant in early Spring and twine around suitable supports.

*Dormancy.*—Generally — The present hop variety emerges from dormancy approximately one week later than the commercial variety 'Zeus' (unpatented); and approximately one week earlier than the variety 'Galena' (unpatented) at the same geographical location. In this regard, the commercial variety 'Zeus' (unpatented) emerges approximately the third or fourth week of March at the same geographical location in Washington, while 'Galena' does not emerge until the first week of April.

*Shoot growth rate.*—Generally — Considered average when compared against other common commercial varieties. The present variety, however, is slower than the hop variety 'Nugget' (unpatented) at the same geographical location.

*Vine stems.*—Shape — Generally considered to be hexagonal.

*Vine stems.*—Color — Green with the corners of the hexagonal shaped vine having a light purplish brown stripe similar to the commercial variety 'Zeus' (unpatented). This color, however, appears less pronounced. This purplish brown color is not particularly distinctive of the present variety.

*Stems.*—Growth — Average, as compared to other commercial varieties.

*Stems.*—Size — Typically about ⅜ inch in diameter when measured approximately 6 feet above ground level.

*Cultural measures.*—Generally — The present variety is considered to be a low trellis vine which self-trains, that is, the vines are allowed to grasp support strings to begin upward growth. The present variety, as a general matter, can reach the top of a low trellis in approximately 4 weeks after self-training which typically occurs in late May. In the event that the variety is grown on a conventional high trellis, early May training may be required. Low trellis heights stand typically at approximately 10 feet and normal trellis heights are typically about 18 feet.

*Stipule growth direction.*—Generally — Considered to be downward.

*Plant shape.*—Generally — Columnar on low trellis arrangements. Fusiform when grown on high trellis arrangements.

LEAVES

*Leaves.*—Generally — The leaves of the 'Summit' variety are borne in pairs at each node on the main bine.

*Leaves.*—Position — Considered opposite.

*Stipules.*—Location — Typically at the petiole base of each leaf.

*Stipules.*—Arrangement — Considered interpetiolar.

*Leaves.*—Size — Considered average as compared to other common varieties.

*Leaf.*—Width — Approximately 6–7 inches in width.

*Leaf.* —Shape — Cordate and having 3–5 palmate lobes and further having palmate venation.

*Leaf margin.* —Shape — Slightly serrated, and moderately dentate.

*Sinus-Clefts.*—Shape — Considered moderately cut.

*Leaf color.*—Upper surface — Dark Green (RHS 137A).

*Leaf color.*—Lower surface — Lighter Green (RHS 137C).

*Leaf petiole.* —Color — Green (RHS 146C).

*Leaf petiole.*—Color — Upper surface only — Green (RHS 146C). This green coloration is distinctly different from that of the 'Zeus' hop plant (unpatented) which displays a purple shading on the upper side of the petiole.

*Leaf petiole.*—Position — Extends from the main bine at approximately 90 degree angle and is slightly reflexed.

*Petioles.*—Shape — Slightly channeled and having a flat surface on the upper surface.

*Leaves.*—Upper surface texture — Rough. As a general matter, stiff fine hairs appear on the upper surface of the leaf. This creates a dull appearance and a rough texture.

*Surface characteristics.*—Lower surface of leaf — Many disc-shaped yellowish resin glands appear on the lower surface.

CONES

*Generally.* —Inflorescences of the present variety 'Summit' begin to appear on the bines in early July and mature during the second to third week of September under the ecological conditions prevailing in Central Washington. As the respective inflorescences mature, they form a cone-like structure or strobile and which is best seen in FIG. 1.

*Form.*—the present variety develops inflorescence on a cranked axis and typically in even pairs, or clusters. The cones on the present variety develop on laterals from the top of the plant to a location approximately 24 inches above ground level.

*Strig.*—Generally — Considered compact with a model diameter.

*Aroma.*—Generally — Considered moderate, but pleasant.

*Cone length.*—Approximately 1.25 to about 1.40 inches when grown under the ecological conditions prevailing in Central Washington.

*Cone tip.*—Shape — Bluntly pointed.

*Cone shape.*—Ovoid in shape.

*Compactness.*—Considered tight and semi-dense for the present variety.

*Bract tip.*—Shape — Considered cuspidate.

*Bracteole.*—Shape — Considered acute to deltoid.

*Central rachis.*—Form — Compact, but not considered as thick as compared to the strig of the common commercial variety 'Zeus' (unpatented).

*Lupulin glands.*—Numbers — The cone of the present variety contains numerous lupulin glands. In this regard, it should be understood that average numbers of glands are usually impossible to quantify. The numbers of lupulin glands will vary from year to year based upon the weather and a multitude of other environmental and cultural factors. Further, it should be understood that there are a large number of individual glands in each cone, and significant variations between cones on the same plant. Generally speaking, it is clear that the present variety has numerous glands because it is characterized as a high alpha variety.

*Date of maturity.*—considered to be middle to late as compared to other common hop varieties grown in Central Washington.

*Cone shape.*—Uniformity — Considered uniform.

*Harvestability.*—Generally — The hop cones of the present variety 'Summit' are well adapted for mechanical harvesting because of their compactness and ovoid shape. The cones of the present variety are not shattered during harvest.

*Lupulin glands.* —Shape — Considered globular and having a golden yellow color (RHS 2A) which is not particularly distinctive of the present variety. This color is somewhat variable based upon environmental, and other cultural practices.

*Bract tip position.*—Considered appressed, however some bracts are slightly everted at full maturity.

*Yield per acre.*—Approximately 2,000 to about 2,300 pounds on average. However, this yield is contingent upon temperature, soil conditions and cultural practices and is therefore not distinctive of the present variety.

*Cone bracteole.*—Color — Green (RHS 145A).

*Cone bract.*—Color — Green (RHS 145C).

ANALYTICAL DATA OF THE CONES

*Generally.*—The analytical data as provided hereinafter of the cones have been gathered from cones having a cone moisture of approximately 8%.

*Percentage of alpha-acids as calculated in a base.*—About 18–19% as determined by the ASBC Spectrophotometric method.

*Percentage of beta-acids as calculated in a bale.*—Approximately 3.3–4.3% as calculated by the ASBC Spectrophotometric method.

*Alpha/beta acid ratio.*—About 5.0 to about 6.0.

*Cohumulone (%of alpha-acids).—About* 32.5%.

*Colupulone (% of beta-acids).—Approximately* 54%.

*Storage characteristics.*—The cones of the present variety experience a 12% transformation of alpha acids after about 6 months of storage at 22° C. In relative comparison to other common varieties, this rate of transformation is less than the best storing high alpha acid commercial varieties such as 'Galena' and 'Nugget' (both unpatented).

*Total oil content.*—About 1.5 milliliters per 100 grams.

*Humulene (%of total oils).*—Approximately 15%.

*Caryophyllene (% of total oils).*—Approximately 10%.

*Humulene/caryophyllene ratio.*—Approximately 1.5.

*Farnesene (% of total oils).*—0.

*Myrcene (%of total oils).*—Approximately 485.

*Lupulin (%of total cone weight).*—Approximately 30%.

*Ploidy.* —The genetic make up of 'Summit' is diploid. In this regard, the mother is diploid and the father is diploid.

*Disease resistance.* —The variety 'Summit' appears to be moderately susceptible to hop downy mildew fungus. 'Summit' appears to be resistant to the strains of powdery mildew fungus typically found in the Yakima Valley of Central Washington. 'Summit' also appears tolerant to strains of Verticillium Wilt and other virus diseases found in U.S. growing areas. This variety also appears tolerant to the major soil borne pests that affect hops including Phytophthora root rot.

*Regional adaptation.* —The 'Summit' variety of hop appears to be adapted to the drier growing regions of Washington State, especially the Yakima Valley of Central Washington.

*Life expectancy.* —Unknown.

Although the new variety of hop possesses the desired characteristics when grown under the ecological conditions prevailing in the Yakima Valley of Central Washington, it should be understood that variations of the usual magnitude and characteristics incident to changing and growing conditions, fertilization, pruning, pest control and horticultural management are to be expected.

Having thus described and illustrated my new variety of hop, what I claim is new, and desire to secure by Plant Letters Patent is:

1. A new and distinct variety of hop substantially is illustrated and described and which is characterized principally as to novelty by being semi-dwarf in nature; having a high percentage of alpha-acids, high alpha/beta ratio and excellent storage stability of alpha-acids; and which is mature for harvesting approximately 10 to 20 September under the ecological conditions prevailing in the Yakima Valley of Central Washington.

* * * * *

UNITED STATES PATENT AND TRADEMARK OFFICE

CERTIFICATE OF CORRECTION

PATENT NO. : PP 18,039 P3
APPLICATION NO. : 11/236165
DATED : September 18, 2007
INVENTOR(S) : Roger Jeske It is certified that error appears in the above-identified patent and that said Letters Patent is hereby corrected as shown below:

Column 6, line 35, replace “in a base.” with --in a bale.--.

Column 6, line 36, replace “About 18-19%” with --About 18-19.5%--.

Column 6, line 56, replace “Approximately 485.” with --Approximately 48%.--.

Signed and Sealed this

First Day of July, 2008

JON W. DUDAS
*Director of the United States Patent and Trademark Office*